United States Patent
Yamagawa et al.

(10) Patent No.: US 11,452,675 B2
(45) Date of Patent: Sep. 27, 2022

(54) DENTAL CURABLE COMPOSITION

(71) Applicant: Tokuyama Dental Corporation, Tokyo (JP)

(72) Inventors: Junichiro Yamagawa, Tokyo (JP); Akiyoshi Mori, Tokyo (JP); Yuko Nagasawa, Tokyo (JP); Takuya Suzuki, Tokyo (JP); Yohei Seya, Tokyo (JP)

(73) Assignee: Tokuyama Dental Corporation, Tokyo (JP)

( * ) Notice: Subject to any disclaimer, the term of this patent is extended or adjusted under 35 U.S.C. 154(b) by 119 days.

(21) Appl. No.: 16/647,045

(22) PCT Filed: Sep. 14, 2018

(86) PCT No.: PCT/JP2018/034298
§ 371 (c)(1),
(2) Date: Mar. 13, 2020

(87) PCT Pub. No.: WO2019/054507
PCT Pub. Date: Mar. 21, 2019

(65) Prior Publication Data
US 2020/0253835 A1 Aug. 13, 2020

(30) Foreign Application Priority Data
Sep. 14, 2017 (JP) .............................. JP2017-176279

(51) Int. Cl.
| | | |
|---|---|---|
| *A61K 6/887* | (2020.01) | |
| *A61K 6/836* | (2020.01) | |
| *A61K 6/833* | (2020.01) | |
| *A61K 6/84* | (2020.01) | |
| *C08F 20/18* | (2006.01) | |
| *C08F 20/56* | (2006.01) | |

(52) U.S. Cl.
CPC .............. *A61K 6/887* (2020.01); *A61K 6/833* (2020.01); *A61K 6/836* (2020.01); *A61K 6/84* (2020.01); *C08F 20/18* (2013.01); *C08F 20/56* (2013.01)

(58) Field of Classification Search
None
See application file for complete search history.

(56) References Cited

U.S. PATENT DOCUMENTS

| | | | | | |
|---|---|---|---|---|---|
| 5,859,089 | A * | 1/1999 | Qian | ...................... | A61K 6/893 523/116 |
| 6,186,791 | B1 * | 2/2001 | Karmaker | .............. | A61C 13/30 433/220 |
| 6,281,271 | B1 * | 8/2001 | Rumphorst | ............ | A61K 6/887 523/211 |
| 8,137,103 | B1 * | 3/2012 | Freilich | ................ | A61C 8/0048 433/172 |
| 9,023,916 | B2 * | 5/2015 | Blomker | ................ | A61K 6/836 523/115 |
| 9,833,387 | B2 * | 12/2017 | Plaumann | ................ | A61K 6/17 |
| 2003/0134933 | A1 * | 7/2003 | Jin | ........................... | A61K 6/54 523/115 |
| 2006/0252845 | A1 * | 11/2006 | Ruppert | ................. | A61K 6/893 523/115 |
| 2010/0081728 | A1 * | 4/2010 | Uchida | .................. | A61K 6/884 523/105 |
| 2012/0082958 | A1 * | 4/2012 | Blomker | ................. | A61K 6/17 433/219 |

(Continued)

FOREIGN PATENT DOCUMENTS

| | | | |
|---|---|---|---|
| EP | 1974713 | A2 | 10/2008 |
| EP | 2301515 | A1 | 3/2011 |

(Continued)

OTHER PUBLICATIONS

InnovationQ plus, IP.com 16647045 (Year: 2021).*

(Continued)

*Primary Examiner* — Peter A Salamon
(74) *Attorney, Agent, or Firm* — Rankin, Hill & Clark LLP

(57) ABSTRACT

A dental curable composition which comprises a radically polymerizable monomer component (A), a polymerizing catalyst (B) and an inorganic granular material (C), characterized in that:
the radically polymerizable monomer component (A) contains a bifunctional monomer (A-1) represented by the following formula (α), $$R_P\text{—}SP^1\text{—}R_P \qquad (\alpha)$$

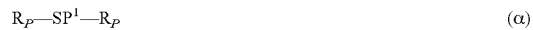

where, $R_P$ is a radically polymerizable group represented by $CH_2=C(R)\text{—}COO\text{—}$ or $CH_2=C(R)\text{—}CONH\text{—}$, wherein R is a hydrogen atom or a hydrocarbon group having 1 to 3 carbon atoms, and $SP^1$ is a hydrocarbon group having 5 to 15 carbon atoms, and the content of the bifunctional monomer (A-1) in the radically polymerizable monomer component (A) is 5 to 40% by mass under a condition that the content of a diluting monomer (A-2) represented by the following formula (β), $$R_P\text{—}SP^2\text{—}R_P \qquad (\beta)$$

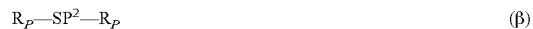

where, $R_P$ is as defined in the above formula (α), and $SP^2$ is an aliphatic hydrocarbon group different from $SP^1$, an oxygen-containing aliphatic hydrocarbon group having not less than 2 oxygen atoms, or an oxygen-containing aromatic hydrocarbon group having not less than 3 oxygen atoms, is zero or not more than 10% by mass.

10 Claims, No Drawings

(56) References Cited

U.S. PATENT DOCUMENTS

| | | | |
|---|---|---|---|
| 2014/0302448 A1* | 10/2014 | Cassalia | A61C 7/20 433/9 |
| 2016/0235631 A1 | 8/2016 | Nojiri | |
| 2016/0346018 A1* | 12/2016 | Gregory | A61B 17/7233 |
| 2020/0253835 A1* | 8/2020 | Yamagawa | A61K 6/836 |

FOREIGN PATENT DOCUMENTS

| | | |
|---|---|---|
| JP | 2014214122 A | 11/2014 |
| JP | 2016-525150 A | 8/2016 |
| JP | 2017055796 A | 3/2017 |
| WO | 2014/172716 A1 | 10/2014 |
| WO | 2015/052913 A1 | 4/2015 |
| WO | 2017/154850 A1 | 9/2017 |

OTHER PUBLICATIONS

TCD di HEA and UDMA AND TEDMA Google scholar search (Year: 2021).*

Extended European Search Report (EESR) dated Apr. 21, 2021 issued in the corresponding European Patent Application No. 18857163.2.

Lauvahutanon et al., "Mechanical properties of composite resin blocks for CAD/CAM", Dental Materials Journal 2014, vol. 33 (5), pp. 705-710; Cited in the specification.

Huang et al., "Physical and chemical properties of an antimicrobial Bis-GMA free dental resin with quaternary ammonium dimethacrylate monomer", Journal of the Mechanical Behavior of Biomedical Materials, 2016, vol. 56, pp. 68-76; Cited in ISR.

International Search Report (ISR) issued in PCT/JP2018/034298 dated Nov. 13, 2018.

* cited by examiner

DENTAL CURABLE COMPOSITION

TECHNICAL FIELD

This invention relates to a dental curable composition. More specifically, the invention relates to a dental curable composition that can be favorably used as a dental resin block that is to be cut for preparing a dental prosthetic by cutting.

BACKGROUND ART

Dental curable compositions, usually, comprise a polymerizable monomer (monomer), a filler and a polymerization initiator as chief components, and are used as composite resins, hard resins, artificial teeth, cements and resins for use by being cut. The dental curable compositions are widely used as dental materials owing to their easiness of handling and low degree of harm to the living bodies. As compared to other materials such as metals and ceramics, however, the dental curable compositions are not still sufficient from the standpoint of mechanical strength for being used in severe environments in oral cavities and, specifically, in long-term wet environments. Therefore, the dental curable compositions must be further improved even from the standpoint of still other requirements such as aesthetic appearance and workability.

According to a non-patent document 1, a composite resin block for a dental CAD/CAM system exhibits a bending strength equivalent that of a ceramic material. In terms of the three-point bending strength after dipped in water for 7 days, however, the ceramic material is not affected by the dipping in water. Whereas, the composite resin block for the dental CAD/CAM system shows its three-point bending strength that is decreased down to about 80% of its initial value. Although study has been vigorously forwarded in an attempt to improve the initial properties, almost no study was so far conducted in regard to solving the problem of a decrease in the bending strength after the resin block has absorbed water simulating the oral cavity. Here, the dental CAD/CAM system is a system made up of a plurality of equipment used for designing and working restorative materials and prosthetic materials that are to be placed in the oral cavity, the equipment being controlled based on a computer technology such as CAD and CAM.

PRIOR ART DOCUMENT

Non-Patent Document

Non-patent document 1: Dental Materials Journal 2014; 33(5): 705-710

OUTLINE OF THE INVENTION

Problems that the Invention is to Solve

The problem that the invention is to solve is to provide a dental curable composition that can be used for the production of a cured body that maintains the initial strength even after dipped in water.

Means for Solving the Problems

The present inventors have conducted a keen study in order to solve the above-mentioned problems. As a result, the inventors have discovered the fact that upon adding a specific polymerizable monomer in a specific amount, there can be obtained a curable composition that provides a cured body that has a large strength and is capable of minimizing a decrease in the strength even after dipped in water, and have thus completed the present invention.

That is, according to the present invention, there is provided a dental curable composition which includes a radically polymerizable monomer component (A), a polymerizing catalyst (B) and an inorganic granular material (C), characterized in that:

the radically polymerizable monomer component (A) contains a bifunctional monomer (A-1) represented by the following formula (α),

where, $R_P$ is a radically polymerizable group represented by $CH_2=C(R)-COO-$ or $CH_2=C(R)-CONH-$, wherein R is a hydrogen atom or a hydrocarbon group having 1 to 3 carbon atoms, and $SP^1$ is a hydrocarbon group having 5 to 15 carbon atoms, and the content of the bifunctional monomer (A-1) in the radically polymerizable monomer component (A) is 5 to 40% by mass under a condition that the content of a diluting monomer (A-2) represented by the following formula (β),

where, $R_P$ is as defined in the above formula (α), and $SP^2$ is an aliphatic hydrocarbon group different from $SP^1$, an oxygen-containing aliphatic hydrocarbon group having not less than 2 oxygen atoms, or an oxygen-containing aromatic hydrocarbon group having not less than 3 oxygen atoms, is zero or not more than 10% by mass.

In the dental curable composition of the present invention, it is desired that:

(1) In the bifunctional monomer (A-1), the group $SP^1$ has a hydrocarbon group on the side chain thereof;

(2) In the bifunctional monomer (A-1), the group $SP^1$ has an aliphatic hydrocarbon ring or an aromatic ring on the main chain thereof;

(3) The radically polymerizable monomer component (A) contains a basic monomer (A-3) in an amount of 45 to 95% by mass, the basic monomer (A-3) being a radically polymerizable monomer other than (A-1) or (A-2) and containing 2 to 6 radically polymerizable groups and, further, having, in the main chain thereof, a molecular structure in which at least two of the radically polymerizable groups are coupled together via a crosslinking group that has an aromatic ether bond, an aromatic ketone bond, an amide bond or an urethane bond; and (4) The polymerizing catalyst (B) is contained in an amount of 0.01 to 5 parts by mass per 100 parts by mass of the radically polymerizable monomer component (A), and the inorganic granular material (C) is contained in an amount of 100 to 2000 parts by mass per 100 parts by mass of the radically polymerizable monomer component (A).

According to the present invention, further, there is provided a cured body of the dental curable composition.

In the cured body of the invention, it is desired that:

(1) The cured body is used as a dental resin that is to be used by being cut;

(2) The cured body has a bending strength of not less than 220 MPa after it is dipped in water of 37° C. for 7 days; and (3) The cured body, after it is dipped in water of 37° C. for 7 days, has a bending strength which is not less than 95% of the initial bending strength thereof.

Effects of the Invention

When cured, the dental curable composition of the present invention exhibits a large bending strength and minimizes a decrease in the strength even after it is dipped in water. Namely, the dental curable composition of the present invention makes it possible to produce a cured body that maintains its initial strength even under wet conditions. Specifically, the cured body of the dental curable composition of the present invention can be effectively used as a dental crown restorative in the molar portion on where a large occlusal pressure will be exerted. Namely, the cured body of the dental curable composition of the invention can be favorably used as a dental resin material that is to be cut for producing the dental crown restorative by the cutting work.

MODES FOR CARRYING OUT THE INVENTION

<Radically Polymerizable Monomer Component (A)>

As the radically polymerizble functional group (hereinafter often called polymerizable functional group) possessed by the radically polymerizable monomr component (A) of the present invention, there can be exemplified a (meth) acrylic acid ester group, a (meth)acrylamide group, a vinyl ester group, a vinyl ether group and a styryl group. When a plurality of polymerizable functional groups are included in a molecule, the polymerizable functional groups in the molecule may be the same or different.

From the standpoint of the biological safety, the polymerizable functional group should desirably be a (meth) acrylic acid ester type polymerizable monomer having a (meth)acrylic acid ester group or a (meth)acrylamide derivative having a (meth)acrylamide group. From the standpoint of favorably attaining the polymerization, however, it is most desired to use the (meth)acrylic acid ester type polymerizable monomer. In the present invention, the expression "(meth)acryl" includes both methacryl and acryl.

<Bifunctional Monomer (A-1)>

The bifunctional monomer (A-1) of the present invention can be represented by the following formula (α), $$R_P—SP^1—R_P \quad (\alpha)$$

where, $R_P$ is a radically polymerizable group represented by $CH_2=C(R)—COO—$ or $CH_2=C(R)—CONH—$, wherein R is a hydrogen atom or a hydrocarbon group having 1 to 3 carbon atoms, and $SP^1$ is a hydrocarbon group having 5 to 15 carbon atoms.

The bifunctional monomer (A-1) has a specifically high effect for suppressing the infiltration of water, has a low viscosity and excels in workability.

The hydrocarbon group $SP^1$ (hereinafter often called spacer) in the bifunctional monomer (A-1) may be a straight chain or a branched chain but is preferably the branched chain having side chains. It is, further, desired that the hydrocarbon group $SP^1$ has an alicyclic hydrocarbon or an aromatic ring on the main chain thereof. It is presumed that the above molecular structure suppresses the water from infiltrating into gaps formed among the molecules owing to the steric hindrance.

The hydrocarbon group $SP^1$ has, preferably, 5 to 8 carbon atoms when it is an alkane and has, preferably, 8 to 12 carbon atoms when it is an alicyclic hydrocarbon or an aromatic ring.

The bifunctional monomer (A-1) is contained in the component (A) in an amount of 5 to 40% by mass, preferably, 10 to 25% by mass and, most preferably, 10 to 20% by mass.

The bifunctional monomer (A-1) highly effectively suppresses the infiltration of water yet having a low viscosity and should, therefore, be a compound represented by the following general formula (1).

[Chemical 1]

General formula (1)

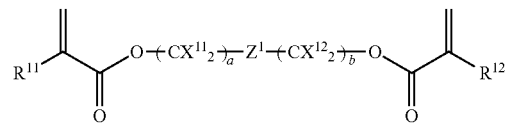

In the general formula (1), the portions represented by $CH_2=C(R^{11})—COO—$ and $CH_2=C(R^{12})—COO—$ are radically polymerizing functional groups $R_P$, and $R^{11}$ and $R^{12}$ are hydrogen atoms or hydrocarbon groups (alkyl groups) having 1 to 3 carbon atoms and, preferably, methyl groups.

Further, the group between the above radically polymerizing functional groups $R_P$ is the spacer ($SP^1$).

In the group $SP^1$, $X^{11}$ and $X^{12}$ may be the same or different and are hydrogen atoms or alkyl groups having 1 to 5 carbon atoms bonded as substituents to the methylene groups. The alkyl groups represent side chains of the group $SP^1$.

Further, a and b representing the numbers of $(CX^{11})_2$ and $(CX^{12})_2$ are, respectively, integers of 0 to 10 and, preferably, 1 to 3. The sum of a and b is 15 at the greatest. Here, $X^{11}$ and $X^{12}$ that are present in plural numbers may be the groups that are different from each other.

$Z^1$ represents a crosslinking bond, a divalent aliphatic hydrocarbon ring group or a divalent aromatic ring group. These aromatic hydrocarbon ring group and divalent aromatic ring group are represented by the following general formula (2).

[Chemical 2]

General formula (2)

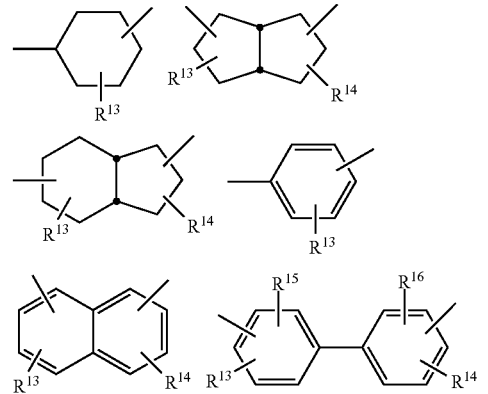

-continued

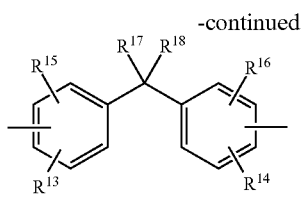

In the above general formula (2), $R^{13}$ to $R^{18}$ may be the same or different and are hydrogen atoms or alkyl groups. Here, the number of carbon atoms of the alkyl groups must be within a range of 5 to 15 which is the total number of carbon atoms of the group $SP^1$.

$Z^1$ is represented, preferably, by the following general formula (3).

[Chemical 3]

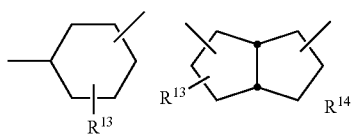

General formula (3)

In the general formula, $R^{13}$, $R^{14}$ and $R^{15}$ represent hydrogen atoms or hydrocarbon groups having 1 to 5 carbon atoms and, preferably, hydrogen atoms or methyl groups which may be the same or different.

The bifunctional monomer (A-1) is, more preferably, any compound represented by the following general formula (4).

[Chemical 4]

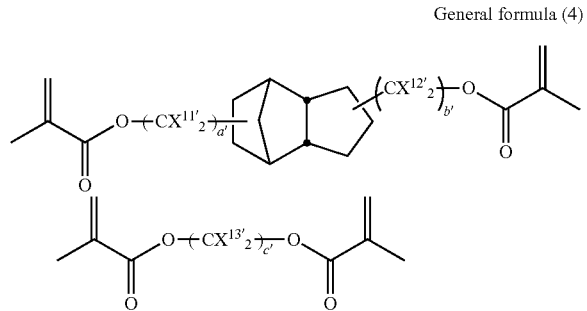

General formula (4)

In the above general formula (4), $X^{11'}$, $X^{12'}$ and $X^{13'}$ are hydrogen atoms or methyl groups which may be different in the same recurring unit.

a' is an integer of 1 to 3,
b' is an integer of 1 to 3,
the sum of a' and b' is an integer of 2 to 6, and
c' is an integer of 2 to 6.

Concrete and preferred examples of the bifunctional monomer (A-1) include:
1,5-Pantanediol di(meth)acrylate,
1,6-Hexanediol di(meth)acrylate,
1,9-Nonanediol di(meth)acrylate,
1,10-Decanediol di(meth)acrylate,
Neopentyl glycol di(meth)acrylate,
Tricyclodecanedimethanol di(meth)acrylate, and
2,2-Bis((meth)acryloyloxyphenyl)propane.

Particularly preferred examples include:
1,6-Hexanediol di(meth)acrylate,
Neopentyl glycol di(meth)acrylate,
Tricyclodecanedimethanol di(meth)acrylate, and
1,9-Nonanediol di(meth)acrylate.
Most preferred examples include:
Neopentyl glycol di(meth)acrylate, and
Tricyclodecanedimethanol di(meth)acrylate.
These polymerizable monomers can be used in a single kind or in combination.

<Diluting Monomer (A-2)>

The diluting monomer (A-2) of the invention can be represented by the following formula (β), $$R_P\text{—}SP^2\text{—}R_P \quad (\beta)$$

where, $R_P$ is as defined in the above formula (α), and $SP^2$ is an aliphatic hydrocarbon group different from $SP^1$, an oxygen-containing aliphatic hydrocarbon group having not less than 2 oxygen atoms, or an oxygen-containing aromatic hydrocarbon group having not less than 3 oxygen atoms.

The diluting monomer (A-2) is an excellent monomer that is usually used for the dental curing compositions. Upon suppressing the amount of the polymerizable monomer of such a structure to lie within the above range, it is presumed that the molecules exhibit decreased mobility and the water is suppressed from infiltrating into the cured body of the dental curable composition of the invention.

It is desired that the group $SP^2$ (hereinafter often called spacer) contains at least 2 oxyalkylene groups when it is an oxygen-containing aliphatic hydrocarbon group and contains at least 3 oxyalkylene groups when it is an oxygen-containing aromatic hydrocarbon group. The oxyalkylene groups may be the same groups or different groups. The oxyalkylene group may have a substituent. The oxyalkylene group is, preferably, an oxyalkylene group having 2 to 4 carbon atoms, and specifically an oxyethylene group or an oxypropylene group.

The amount of the diluting monomer (A-2) relative to the monomer component (A) is zero or not more than 10% by mass, preferably, zero or not more than 5% by mass and, most preferably, zero.

It is desired that the monomer component (A-2) is a compound represented by the following general formula (5) or the general formula (6).

[Chemical 5]

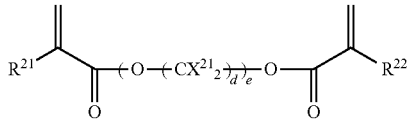

General formula (5)

In the general formula (5), the portions represented by $CH_2=C(R^{21})$—COO— and $CH_2=C(R^{22})$—COO— are radically polymerizing functional groups $R_P$, and $R^{21}$ and $R^{22}$ are hydrogen atoms or hydrocarbon groups having 1 to 3 carbon atoms and, preferably, methyl groups.

Further, the group between the above radically polymerizing functional groups $R_P$ is the spacer ($SP^2$). In the group $SP^2$, $X^{21}$ may be different in the same recurring unit and is a hydrogen atom or an alkyl group having 1 to 5 carbon atoms and, preferably, is a hydrogen atom or a methyl group. When $X^{21}$ is the alkyl group, this alkyl group represents the side chain of $SP^2$.

d is an integer of 1 to 4 and, preferably, an integer of 1 to 3, which may be different in the same recurring unit.

e is a number of 3 to 30 and, preferably, a number of 3 to 10. The number of 3 is an average number.

Here, in the general formula (5), the number of oxygen atoms in the group $SP^2$ is determined depending on the number of e. In the general formula (5), for example, when e is 3, there are 3 oxygen atoms in the parenthesis. Among them, one belongs to the portion of the radically polymerizable functional group $R_P$ represented by $CH_2=C(R^{21})$—COO— and $CH_2=C(R^{22})$—COO—. Therefore, there are 2 oxygen atoms in the group $SP^2$.

[Chemical 6]

General formula (6)

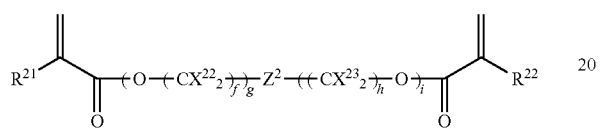

In the general formula (6), the portions represented by $CH_2=C(R^{21})$—COO— and $CH_2=C(R^{22})$—COO— are radically polymerizable functional groups $R_P$, and $R^{21}$ and $R^{22}$ are hydrogen atoms or hydrocarbon groups having 1 to 3 carbon atoms and, preferably, methyl groups.

Further, the group between the above radically polymerizable functional groups $R_P$ is the spacer ($SP^2$). In the group $SP^2$, $X^{22}$ and $X^{23}$ may be different in the same recurring unit and are hydrogen atoms or alkyl groups having 1 to 5 carbon atoms and, preferably, hydrogen atoms or methyl groups. When $X^{22}$ and $X^{23}$ are the alkyl groups, these alkyl groups represent the side chains of $SP^2$.

f is an integer of 1 to 4 and, preferably, an integer of 1 to 3.

g is a number of 3 to 30 and, preferably, a number of 3 to 15.

h is an integer of 1 to 4 and, preferably, an integer of 1 to 3.

i is a number of 1 to 30 and, preferably, a number of 3 to 15.

The sum of g and i is a number of 3 to 30 and, preferably, a number of 6 to 18. The numbers of g and i are average values, respectively.

$Z^2$ is a divalent oxygen-containing aliphatic hydrocarbon ring group or a divalent oxygen-containing aromatic ring group. The oxygen-containing aliphatic hydrocarbon group and the oxygen-containing aromatic ring group can be represented by the following general formula (7).

[Chemical 7]

General formula (7)

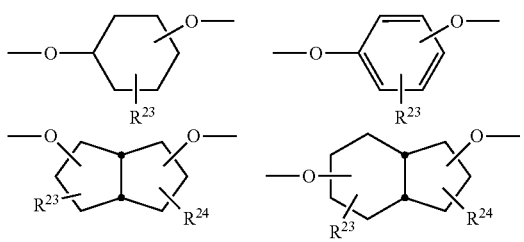

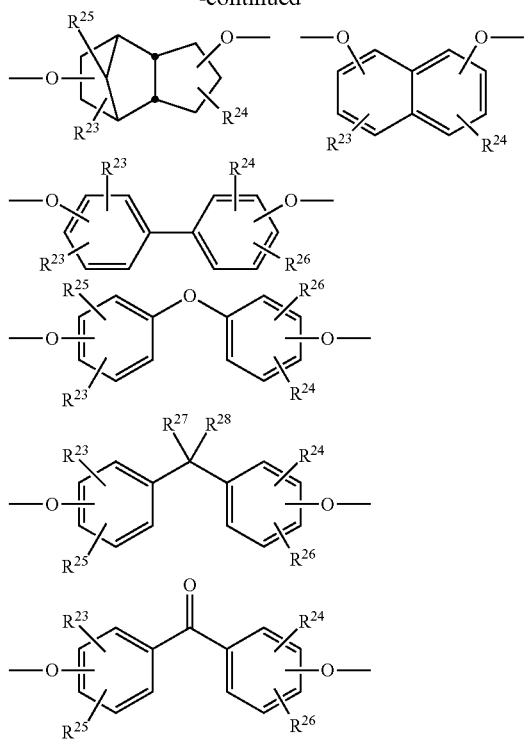

In the above general formula (7), $R^{23}$, $R^{24}$, $R^{25}$, $R^{26}$, $R^{27}$ and $R^{28}$ are hydrogen atoms or hydrocarbon groups having 1 to 5 carbon atoms and, preferably, are hydrogen atoms or methyl groups which may be the same or different.

$Z^2$ is, desirably, the one represented by the following general formula (8).

[Chemical 8]

General formula (8)

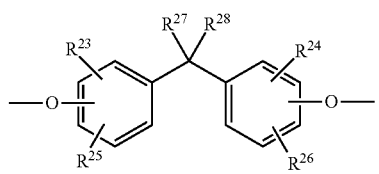

In the above general formula (8), $R^{23}$, $R^{24}$, $R^{25}$, $R^{26}$, $R^{27}$ and $R^{28}$ are hydrogen atoms or hydrocarbon groups having 1 to 5 carbon atoms and, preferably, are hydrogen atoms or methyl groups which may be the same or different.

Here in the general formula (6), the number of oxygen atoms in the group $SP^2$ is determined depending on the total number of g and i and on the number of oxygen atoms possessed by $Z^2$. For example, when the total number of g and i is 3, and $Z^2$ is the one expressed by the general formula (8), there are 3 oxygen atoms in the parenthesis in the general formula (6). Among them, two belong to the portions of the radically polymerizable functional groups $R_P$ represented by $CH_2=C(R^{21})$—COO— and $CH_2=C(R^{22})$—COO—. Therefore, the remaining one oxygen atom and the two oxygen atoms possessed by $Z^2$ make up three oxygen atoms in the group $SP^2$.

The diluting monomer (A-2) is, more preferably, any compound represented by the following general formula (9).

[Chemical 9]

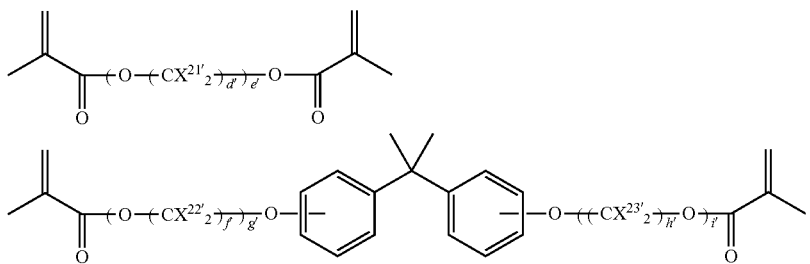

General formula (9)

In the above general formula (9), $X^{21'}$, $X^{22'}$ and $X^{23'}$ are hydrogen atoms or methyl groups which may be different in the same recurring unit.

d', f' and h' are integers of 1 to 3.

e' is a number of 3 to 10.

g' and i' are numbers of 3 to 15, and the sum of g' and i' is a number of 6 to 18.

Preferred and concrete examples of the polymerizable monomer (A-2) include:

Triethylene glycol di(meth)acrylate,

Tetraethylene glycol di(meth)acrylate (polyethylene glycol #200 di(meth)acrylate), Nonaethylene glycol dimethacrylate (polyethylene glycol #400 di(meth)acrylate), Tetradecaethylene glycol di(meth)acrylate (polyethylene glycol #600 di(meth)acrylate), Polypropylene glycol #400 di(meth)acrylate, Polypropylene glycol #700 di(meth)acrylate, 2,2-Bis((4-((meth)acryloyloxy)polyethoxy)phenyl) propane (ethylene oxide, 6 mols), 2,2-Bis((4-((meth)acryloyloxy)polyethoxy)phenyl) propane (ethylene oxide, 10 mols), 2,2-Bis((4-((meth)acryloyloxy)polyethoxy)phenyl) propane (ethylene oxide, 17 mols), and 2,2-Bis((4-((meth)acryloyloxy)polyethoxy)phenyl) propane (ethylene oxide, 30 mols).

Particularly preferred examples include:

Triethylene glycol di(meth)acrylate, and 2,2-Bis((4-((meth)acryloyloxy) polyethoxy)phenyl) propane (ethylene oxide, 6 mols).

The most preferred example is:

Triethylene glycol dimethacrylate.

These polymerizable monomers can be used in a single kind or in combination.

Here, the polyoxyalkylene group is of a high molecular structure as obtained by the polymerization of an alkylene glycol, and has a molecular weight profile; i.e., the polyoxyalkylene group may not often be obtained having a single molecular weight. In this case, the recurring unit of the polyoxyalkylene group can be found by calculating the number of the corresponding alkylene oxide units from an average molecular weight thereof. For example, the 2,2-bis ((4-(methacryloyloxy)ethoxy)phenyl)propane (ethylene oxide, 2.6 mols) having a molecular weight of 478 contains 2.6 mols of an ethylene oxide and in which case, $SP^2$ becomes the oxygen-containing aromatic hydrocarbon group having 2.6 oxygen atoms. Therefore, this compound does not represent the monomer (A-2) that must have the oxygen-containing aromatic hydrocarbon group with 3 oxygen atoms.

<Basic Monomer (A-3)>

In addition to containing such polymerizable monomers as the bifunctional monomer (A-1) and the diluting monomer (A-2), the radically polymerizable monomer component (A) contains, as the basic monomer (A-3), a radically polymerizable monomer other than (A-1) and (A-2), the radically polymerizable monomer (A-3) containing 2 to 6 radically polymerizable groups and having a molecular structure in which the radically polymerizable groups are linked together with a crosslinking group having an aromatic ether bond, an aromatic ketone bond, an amide bond or an urethane bond.

The above molecular structure is based on a rigid molecular chain structure yet having a functional group that interacts among the molecules. Therefore, the above molecular structure helps improve the mechanical strength of the cured body of the dental curable composition of the present invention. From the standpoint of attaining a large strength and the effect for suppressing a decrease in the strength after dipped in water, it is desired that component (A-3) is a polymerizable monomer having an aromatic ether bond or an urethane bond between the radically polymerizable groups.

It is desired that the polymerizable monomer (A-3) contains the radically polymerizable groups in a number of 2 to 4.

Further, the radically polymerizable monomer component (A) contains the polymerizable monomer (A-3) in an amount of 45 to 95% by mass, preferably, 70 to 90% by mass and, more preferably, 80 to 90% by mass.

The polymerizable monomer (A-3) is, desirably, a compound represented by the following general formula (10).

[Chemical 10]

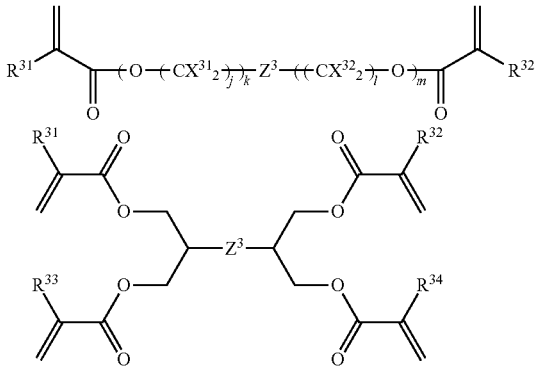

General formula (10)

In the structure of the above general formula (10), the radically polymerizable groups represented by $CH_2=C(R^{31})$—COO—, $CH_2=C(R^{32})$—COO—, $CH_2=C(R^{33})$—COO—, and $CH_2=C(R^{34})$—COO— are called $R_P$, and the portions other than $R_P$ are called $SP^3$ for convenience.

In the above general formula (10), $R^{31}$, $R^{32}$, $R^{33}$ and $R^{34}$ are hydrogen atoms or hydrocarbon groups having 1 to 3 carbon atoms and, preferably, methyl groups.

$X^{31}$ and $X^{32}$ are hydrogen atoms, hydroxyl groups or hydrocarbon groups having 1 to 5 carbon atoms and are, preferably, hydrogen atoms, hydroxyl groups or methyl groups which may be different in the same recurring unit.

j is an integer of 1 to 4 and, preferably, an integer of 1 to 3.

l is an integer of 1 to 4 and, preferably, an integer of 1 to 3.

The sum of k and m is a number of less than 3. The numbers of k and m are average numbers, respectively.

$Z^3$ has any structure selected from the following general formula (11).

[Chemical 11]

General formula (11)

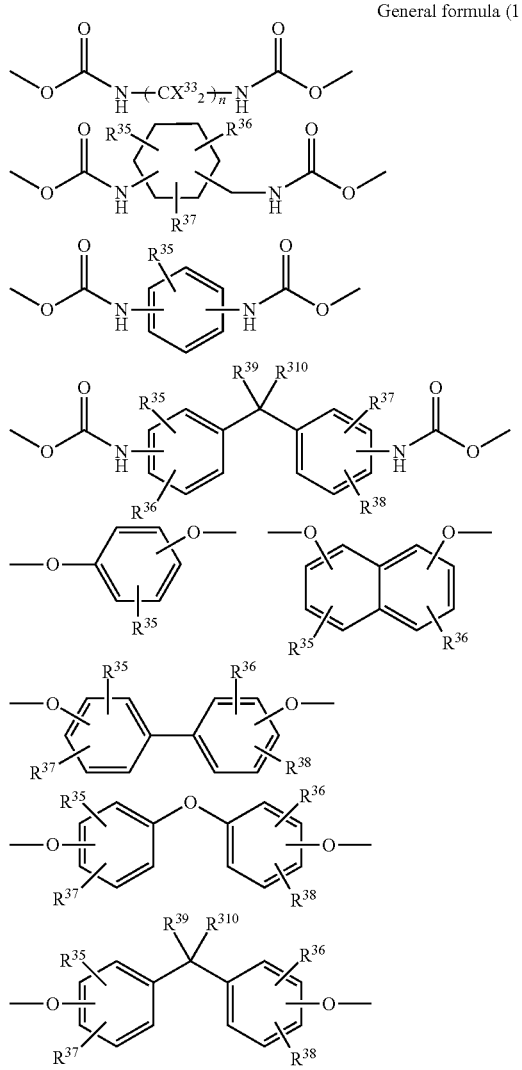

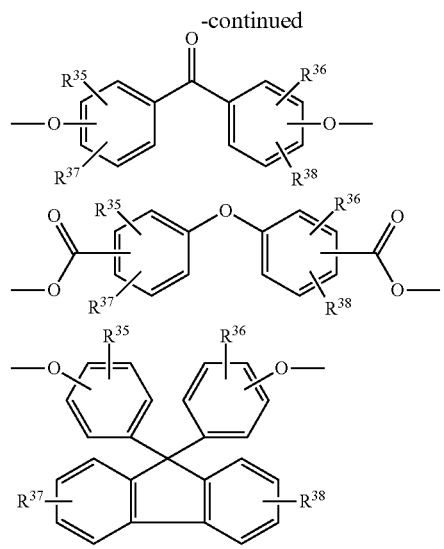

In the above general formula (11), $X^{33}$ is a hydrogen atom or a hydrocarbon group having 1 to 5 carbon atoms and, preferably, the hydrogen atom or the methyl group which may be different in the same recurring unit.

n is an integer of 1 to 15 and, preferably, an integer of 3 to 6.

$R^{35}$, $R^{36}$, $R^{37}$, $R^{38}$, $R^{39}$ and $R^{310}$ are hydrogen atoms or hydrocarbon groups having 1 to 5 carbon atoms and, preferably, hydrogen atoms or methyl groups which may be the same or different.

$Z^3$, preferably, has the structure of the following general formula (12).

[Chemical 12]

General formula (12)

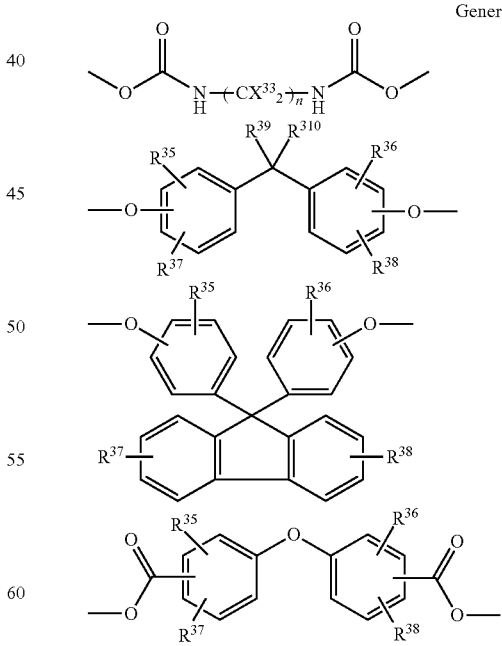

In the above general formula (12), $X^{33}$ is a hydrogen atom or a hydrocarbon group having 1 to 5 carbon atoms and, preferably, the hydrogen atom or the methyl group which may be different in the same recurring unit.

n is an integer of 1 to 15 and, preferably, an integer of 3 to 6.

$R^{35}$, $R^{36}$, $R^{37}$, $R^{38}$, $R^{39}$ and $R^{310}$ are hydrogen atoms or hydrocarbon groups having 1 to 5 carbon atoms and, preferably, are hydrogen atoms or methyl groups which may be the same or different.

The basic monomer (A-3), more desirably, is any compound represented by the following general formula (13).

[Chemical 13]

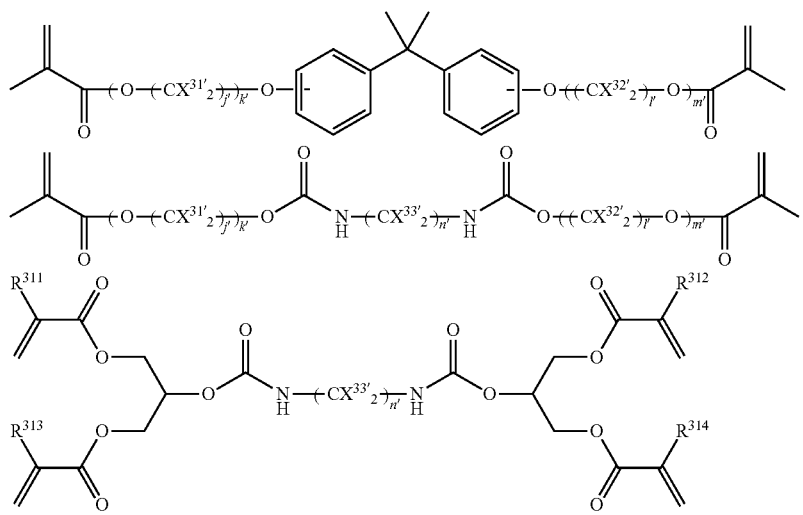

General formula (13)

In the above general formula (13), $R^{311}$, $R^{312}$, $R^{313}$ and $R^{314}$ are hydrogen atoms or methyl groups. $X^{31'}$, $X^{32'}$ and $X^{33'}$ are hydrogen atoms, hydroxyl groups or methyl groups which may be different in the same recurring unit.

j' and l' are integers of 1 to 3.

The sum of k' and m' is a number of less than 3. The numbers of k' and m' are average numbers, respectively.

n' is an integer of 1 to 15 and, preferably, an integer of 3 to 6.

Preferred and concrete examples of the polymerizable monomer (A-3) are:

2,2-Bis[4-(meth)acryloyloxyethoxyphenyl]propane, 2,2-Bis[4-(3-(meth)acryloyloxy)-2-hydroxypropoxy-phenyl]propane, 2,2-Bis[(4-((meth)acryloyloxyethoxy)phenyl)propane (ethylene oxide, 2.3 mols), 2,2-Bis[(4-((meth)acryloyloxyethoxy)phenyl)propane (ethylene oxide, 2.6 mols), 5 Dimethacryloxyethoxylated 9,9'-bis[(4-hydroxy(phenyl)]fluorine <aromatic ether bond>, and Diadduct of a (meth)acrylate having an OH group and a diisocyanate compound.

Moreover, concrete examples of the (meth)acrylate having the OH group include:

2-Hydroxyethyl (meth)acrylate,

2-Hydroxypropyl (meth)acrylate,

3-Chloro-2-hydroxypropyl (meth)acrylate, and

Glycerol di(meth)acrylate.

Concrete examples of the diisocyanate compound include:

Hexamethylene diisocyanate,

Trimethylhexamethylene diisocyanate,

Diisocyanate methylcyclohexane,

Isophorone diisocyanate, and

Mehtylenebis(4-cyclohexyl isocyanate).

Concrete examples of the diadduct include:

1,6-Bis[(meth)acrylethyloxycarbonylamino]-trimethyl-hexane, and

N,N'-(2,2,4-trimethylhexamethylene)bis(2-aminocarboxy-propane-1,3-diol) tetra(meth)acrylate.

Concrete examples of the polymerizable monomer (A-3) that are particularly preferred are:

2,2-Bis[4-(3-(meth)acryloyloxy)-2-hydroxypropoxy-phenyl]propane, 2,2-Bis[(4-((meth)acryloyloxyethoxy)phenyl]propane (ethylene oxide, 2.6 mols), and 1,6-Bis[(meth)acrylethyloxycarbonylamino]trimethyl-hexane.

Concrete examples of the polymerizable monomer (A-3) that are most preferred are:

1,6-Bis(methacrylethyloxycarbonylamino) trimethyl-hexane, and 2,2-Bis(4-methacryloyloxyethoxyphenyl)propane (ethylene oxide, 2.6 mols).

These polymerizable monomers can be used alone or in a combination.

As for a combination of the radically polymerizable monomer component (A), there are selected, 1,6-Hexanediol dimethacrylate (HD), Neopentyl glycol dimethacrylate (NPG), Tricyclodecanedimethanol dimethacrylate (DCP), or 1,9-Nonanediol dimethacrylate (ND), as the bifunctional monomer (A-1), and Triethylene glycol dimethacrylate (TEGDMA), as the diluting monomer (A-2).

There is, further, selected, 1,6-Bis(methacrylethyloxycarbonylamino) trimethyl-hexane (UDMA), or 2,2-Bis(4-methacryloyloxyethoxyphenyl)propane (ethylene oxide, 2.6 mols) (D-2.6E), as the basic monomer (A-3).

It is desired to use the above components in an arbitrary combination. Here, the content of the monomer (A-2) may be zero.

The following combinations are specifically desired.
A combination of HD, UDMA and D-2.6E,
A combination of NPG, UDMA and D-2.6E,
A combination of DCP, UDMA and D-2.6E,
A combination of ND, UDMA and D-2.6E,
A combination of NPG, TEGDMA and UDMA,
A combination of NPG and UDMA, and
A combination of DCP and UDMA.

<Polymerizable Monomers Other than the Bifunctional Monomer (A-1), Diluting Monomer (A-2) and Basic Monomer (A-3)>

In addition to the monomers (A-1), (A-2) and (A-3), the radically polymerizable monomer component (A) used for the dental curable composition of the invention may contain another monomer (A-4) and any further polymerizable monomers within a range in which they do not impair the effects of the present invention.

Concrete examples of the polymerizable monomer (A-4) are as described below.

As the monofunctional radically polymerizable monomer, there can be exemplified:
  Methyl (meth)acrylate,
  Ethyl (meth)acrylate,
  N-butyl (meth)acrylate,
  2-Ethylhexyl (meth)acrylate,
  5 N-lauryl (meth)acrylate,
  N-stearyl (meth)acrylate,
  Tetrafurfuryl (meth)acrylate,
  Glycidyl (meth)acrylate,
  Methoxyethylene glycol (meth)acrylate,
  Methoxydiethylene glycol (meth)acrylate,
  Methoxytriethylene glycol (meth)acrylate,
  Methoxypolyethylene glycol (meth)acrylate,
  Ethoxyethylene glycol (meth)acrylate,
  Ethoxydiethylene glycol (meth)acrylate,
  Ethoxytriethylene glycol (meth)acrylate,
  Ethoxypolyethylene glycol (meth)acrylate,
  Phenoxyethylene glycol (meth)acrylate,
  Phenoxydiethylene glycol (meth)acrylate,
  Phenoxytriethylene glycol (meth)acrylate,
  Phenoxypolyethylene glycol (meth)acrylate,
  Cyclohexyl (meth)acrylate,
  Benzyl (meth)acrylate,
  Isoboronyl (meth)acrylate, and
  Trifluoroethyl (meth)acrylate.

As the monofunctional polymerizable monomer having an acid group, there can be exemplified:
  (Meth)acrylic acid,
  N-(meth)acryloylglycine,
  N-(meth)acryloylaspartic acid,
  N-(meth)acryloyl-5-aminosalicilic acid,
  2-(Meth)acryloyloxyethylhydrogen succinate,
  2-(Meth)acryloyloxyethylhydrogen phthalate,
  2-(Meth)acryloyloxyethylhydrogen maleate,
  6-(Meth)acryloyloxyethylnaphthalene-1,2,6-tricarboxylic acid,
  O-(Meth)acryloyltyrosine,
  N-(Meth)acryloyltyrosine,
  N-(Meth)acryloylphenylalanine,
  N-(Meth)acryloyl-p-aminobenzoic acid,
  N-(Meth)acryloyl-o-aminobenzoic acid,
  P-vinylbenzoic acid,
  2-(Meth)acryloyloxybenzoic acid,
  3-(Meth)acryloyloxybenzoic acid,
  4-(Meth)acryloyloxybenzoic acid,
  N-(meth)acryloyl-5-aminosalicilic acid,
  N-(meth)acryloyl-4-aminosalicilic acid, and
  Compounds thereof whose carboxyl groups are rendered to be acid anhydride groups thereof.

As the monofunctional polymerizable monomer having an acid group, there can be, further, exemplified:
  11-(Meth)acryloyloxyundecane-1,1-dicarboxylic acid,
  10-(Meth)acryloyloxydecane-1,1-dicarboxylic acid,
  12-(Meth)acryloyloxydodecane-1,1-dicarboxylic acid,
  6-(Meth)acryloyloxyhexane-1,1-dicarboxylic acid,
  2-(Meth)acryloyloxyethyl-3'-methacryloyloxy-2'-(3,4-dicarboxybenzoyloxy)propyl succinate,
  4-(2-(Meth)acryloyloxyethyl) trimellitate anhydride,
  4-(2-(Meth)acryloyloxyethyl) trimellitate,
  4-(Meth)acryloyloxyethoxyethyl trimellitate,
  4-(Meth)acryloyloxybutyl trimellitate,
  4-(Meth)acryloyloxyhexyl trimellitate,
  4-(Meth)acryloyloxydecyl trimellitate,
  4-(Meth)acryloyloxybutyl trimellitate,
  6-(Meth)acryloyloxyethylnaphthalene-1,2,6-tricarboxylic acid anhydride,
  6-(Meth)acryloyloxyethylnaphthalene-2,3,6-tricarboxylic acid anhydride,
  4-(Meth)acryloyloyethylcarbonylpropionoyl-1,8-naphthalic acid anhydride,
  4-(Meth)acryloyloxyethylnaphthalene-1,8-tricarboxylic acid anhydride,
  9-(Meth)acryloyloxynonane-1,1-dicarboxylic acid,
  13-(Meth)acryloyloxytridecane-1,1-dicarboxylic acid,
  11-(Meth)acylamideundecane-1,1-dicarboxylic acid,
  2-(Meth)acryloyloxyethyldihydrogen phosphate,
  2-(Meth)acryloyloxyethylphenylhydrogen phosphate,
  10-(Meth)acryloyloxydecyldihydrogen phosphate,
  6-(Meth)acryloyloxyhexyldihydrogen phosphate,
  2-(Meth)acryloyloxyethyl-2-bromoethylhydrogen phosphate,
  2-(Meth)acrylamide ethyl dihydrogen phosphate,
  2-(Meth)acrylamide-2-methylpropanesulfonic acid,
  10-Sulfodecyl (meth)acrylate,
  3-(Meth)acryloxypropyl-3-phosphono propionate,
  3-(Meth)acryloxypropylphosphono acetate,
  4-(Meth)acryloxybutyl-3-phosphono propionate,
  4-(Meth)acryloxybutylphosphono acetate,
  5-(Meth)acryloxypentyl-3-phosphono propionate,
  5-(Meth)acryloxypentylphosphono acetate,
  6-(Meth)acryloxyhexyl-3-phosphono propionate,
  6-(Meth)acryloxyhexylphosphono acetate,
  10-(Meth)acryloxydecyl-3-phsphono propionate,
  10-(Meth)acryloxydecylphosphono acetate,
  2-(Meth)acryloxyethyl-phenyl phosphonate,
  2-(Meth)acryloyloxyethylphosphonic acid,
  10-(Meth)acryloyloxydecylphosphonic acid,
  N-(meth)acryloyl-co-aminopropylsulfonic acid,
  2-(Meth)acryloyloxyethylphenylhydrogen phosphate,
  2-(Meth)acryloyloxyethyl-2'-bromoethylhydrogen phosphate, and
  2-(Meth)acryloyloxyethylphenyl phosphate.

As the monofunctional polymerizable monomer having a hydroxyl group, there can be exemplified:
  2-Hydroxyethyl (meth)acrylate,
  3-Hydroxypropyl (meth)acrylate,
  4-Hydroxybutyl (meth)acrylate,
  6-Hydroxyhexyl (meth)acrylate,
  10-Hydroxydecyl (meth)acrylate,
  Propylene glycol mono(meth)acrylate,
  Glycerol mono(meth)acrylate,
  Erythritol mono(meth)acrylate, N-methylol (meth)acrylamide,
N-hydroxyethyl(meth)acrylamide, and
N,N-(dihydroxyethyl) (meth)acrylamide.

As the bifunctional radically polymerizable monomer, there can be exemplified:
Ethylene glycol di(meth)acrylate,
Diethylene glycol dimethacrylate,
Glycerin dimethacrylate,
Propylene glycol di(meth)acrylate,
Pentaerythritol di(meth)acrylate,
Di[2-(meth)acryloyloxyethyl]hydrogen phosphate,
Di[4-(meth)acryloyloxybutyl]hydrogen phosphate,
3,3,4,4-Hexafluoro-1,5-pentyl dimethacrylate,
2-Hydroxy-1,3-dimethacryloxypropane,
Di[6-(meth)acryloyloxyhexyl]hydrogen phosphate,
Di[8-(meth)acryloyloxyoctyl]hydrogen phosphate,
Di[9-(meth)acryloyloxynonyl]hydrogen phosphate,
Di[10-(meth)acryloyloxydecyl]hydrogen phosphate, and
1,3-Di(meth)acryloyloxypropyl-2-hydrogen phosphate.

As the trifunctional radically polymerizable monomer, there can be exemplified:
Trimethylolpropane tri(meth)acrylate,
Trimethylolethane tri(meth)acrylate,
Pentaerythritol tri(meth)acrylate,
Dipentaerythritol tri(meth)acrylate,
Ethoxylated trimethylolpropane tri(meth)acrylate,
Propoxylated trimethylolpropane tri(meth)acrylate, and
Tris(2-(meth)acryloxyethyl isocyanulate).

As the tetrafunctional radically polymerizable monomer, there can be exemplified tetra(meth)acrylate compounds such as pentaerythritol tetra(meth)acrylate, ethoxylated pentaerythritol tetra(meth)acrylate, propoxylated pentaerythritol tetra(meth)acrylate, and ethoxylated ditrimethylolpropane tetra(meth)acrylate.

The above polymerizable monomers can be all used alone or in combination.

<(B) Polymerization Catalyst>

The dental curable composition of the present invention contains a polymerization catalyst (B). The polymerization catalyst (B) is added to polymerize and cure the radically polymerizable monomer (A). The method of polymerizing the dental curable composition of the invention may rely upon a reaction that uses light energy such as ultraviolet rays or visible light rays (hereinafter photopolymerization), upon a chemical reaction of a peroxide with an accelerator, or upon the use of heat energy (hereinafter thermal polymerization), and any of them can be used. Here, however, it is desired to use a photopolymerization catalyst or a thermal polymerization catalyst from such standpoints that the polymerization can be carried out at any timing utilizing energy such as light or heat fed from the external unit and that the operation is easy. Further, when the dental curable composition of the present invention is cured and is used as a dental resin material that is to be used by being cut, the cured body must have a large thickness and a toned color. With the cured body of this kind, however, it is often difficult to let the ray of light enter into the interior of the dental cured composition. It is, therefore, desired to use the thermal polymerization catalyst. The polymerization catalysts described below should be suitably selected and used depending on the polymerization method that is employed.

For example, as the photopolymerization initiator, there can be used:
Benzoin alkyl ethers such as benzoin methyl ether, benzoin ethyl ether, and benzoin isopropyl ether;
Benzyl ketals such as benzyl dimethyl ketal and benzyl diethyl ketal;
Benzophenones such as benzophenone, 4,4'-dimethylbenzophenone, and 4-methacryloxybenzophenone;
α-Diketones such as diacetyl, 2,3-pentadionebenzyl, camphorquinone, 9,10-phenanthraquinone, and 9,10-anthraquinone;
Thioxanthone compounds such as 2,4-diethoxythioxanthone, 2-chlorothioxanthone and methylthioxanthone; and
Acylphosphine oxides such as bis(2,6-dichlorobenzoyl) phenylphosphine oxide, bis(2,6-dichlorobenzoyl)-2,5-dimethyl-phenylphosphine oxide, bis(2,6-dichlorobenzoyl)-4-propyl-phenylphosphine oxide, bis(2,6-dichlorobenzoyl)-1-naphthyl-phosphine oxide, 2,4,6-trimethylbenzoyldiphenylphosphine oxide, and bis(2,4,6-trimethylbenzoyl) phenylphosphine oxide.

As the photopolymerization initiator, there is often used a reducing agent like:
Tertiary amines such as 2-(dimethylamino)ethyl methacrylate, ethyl 4-dimethylaminobenzoate, and N-methyldiethanolamine;
Aldehydes such as laurylaldehyde, dimethylaminobenzaldehyde, and terephthalaldehyde; and
Sulfur-containing compounds such as 2-mercaptobenzoxazole, 1-decanethiol, thiosalicylic acid and thiobenzoic acid.

As the thermal polymerization initiator, there can be exemplified:
Peroxides such as benzoyl peroxide, p-chlorobenzoyl peroxide, tert-butylperoxy-2-ethyl hexanoate, tert-butylperoxy dicarbonate and diisopropylperoxy dicarbonate;
Azo compounds such as azobisisobutylonitrile;
Boron compounds such as tributylborane, partial oxide of tributylborane, sodium tetraphenylborate, sodium tetrakis(p-fluorophenyl)borate, and triethanolamine salt of tetraphenylboric acid;
Barbituric acids such as 5-butylbarbituric acid, and 1-benzyl-5-phenylbarbituric acid; and
Sulfinates such as sodium benzenesulfinate and sodium p-toluenesulfinate.

Since the invention provides the cured body of a large strength, it is desired to use a peroxide such as benzoyl peroxide.

These polymerization initiators can be used alone or as a mixture of two or more kinds. The polymerization initiator is used in an amount of, desirably, 0.01 to 5 parts by mass per 100 parts by mass of the polymerizable monomer (A).

<(C) Inorganic Granular Material>

The dental curable composition of the present invention contains an inorganic granular material (C). The inorganic granular material (C) is a filler that is added to increase the strength of the cured body of the dental curable composition, to increase the modulus of elasticity thereby to decrease the deflection, to increase abrasion resistance and to suppress the polymerization shrinkage. In addition to the inorganic granular material (C), there can be, further, added, as a filler, an organic granular material or an organic/inorganic composite granular material.

<Amount of the Inorganic Granular Material to be Added>

In a preferred embodiment of the present invention, the amount of the inorganic granular material (C) that is to be added should be determined depending on the object but is, usually, used at a ratio of 100 to 2000 parts by mass per 100 parts by mass of the radically polymerizable monomer component (A). For the use as the dental resin material that is to be used by being cut, which has, usually, been polymerized to a high degree and has poor adhesiveness, it is desired that the inorganic granular material is added in a larger amount so that the silane coupling agent is allowed to easily act thereupon. The inorganic granular material is used at a ratio of, more preferably, 400 to 700 parts by mass and, most preferably, 500 to 600 parts by mass.

<Inorganic Granular Material>

There is no specific limitation on the inorganic granular material (C) that is used for the dental curable composition of the present invention. There can be used any inorganic granular material that has been used as a filler for the conventional curable compositions.

Concretely, there can be used:

Simple metals selected from the transition metals of the Groups I, II, III and IV of the periodic table;

Oxides of these metals and composite oxides thereof;

Glasses containing these metals

Metal salts comprising fluorides, carbonates, sulfates, silicates, hydroxides, chlorides, sulfides and phosphates; and Composite products of these metal salts.

Preferably, there can be used:

Metal oxides such as amorphous silica, quartz, alumina, titania, zirconia, barium oxide, yttrium oxide, lanthanum oxide and ytterbium oxide;

Silica type composite oxides such as silica-zirconia, silica-titania, silica-titania-barium oxide and silica-titania-zirconia;

Glasses such as borosilicate glass, aluminosilicate glass, and fluoroaluminosilicate glass;

Metal fluorides such as barium fluoride, strontium fluoride, yttrium fluoride, lanthanum fluoride and ytterbium fluoride;

Inorganic carbonates such as calcium carbonate, magnesium carbonate, strontium carbonate and barium carbonate; and Metal sulfates such as magnesium sulfate and barium sulfate.

The inorganic granular material (C) can be in the form of a mixture containing any other different materials.

Among them, it is desired that the metal oxide and the silica type composite oxide are those that have been fired at high temperatures in order to obtain a dense material and to suppress a decrease in the strength of the material after it is dipped in water. To improve the effects thereof, further, it is desired to add an oxide of a metal of the Group I of the periodic table, such as sodium in small amounts.

Among the above inorganic granular materials, the granular silica type composite oxide permits the refractive index to be easily adjusted. Moreover, this material contains much silanol groups in the surfaces of the granules thereof and, therefore, enables the surfaces thereof to be easily reformed by using the silane coupling agent or the like agent, offering a particularly desirable advantage.

The above granular materials such as silica-zirconia, silica-titania, silica-titania-barium oxide, and silica-titania-zirconia produce high X-ray contrasts, and are desirable. Moreover, they help provide cured bodies having excellent abrasion resistance. It is, therefore, most desired to use the granular silica-titania and granular silica-zirconia.

<Shape of the Inorganic Granular Materials>

The inorganic granular material (C) of any known shape can be used without limitation for the dental curable composition of the present invention. The inorganic granular materials that can be used will assume various shapes such as spherical shape, nearly spherical shape, amorphous shape, semi-spherical shape, lens-like shape, dented shape, mushroom-like shape, aggregated shape, clustered shape, dimpled shape, plate-like shape or fibrous shape. Since the cured body of the dental curable composition of the present invention has a large strength, it is desired that the inorganic granular material (C) contains the material of amorphous shape and, more desirably, that the inorganic granular material contains those of amorphous shape and spherical shape in combination. The ratio of the amorphous granular material and the spherical granular material is, preferably, 50 to 250 parts by mass of the amorphous granular material and, more preferably, 100 to 150 parts by mass of the amorphous granular material per 100 parts by mass of the spherical granular material.

<Grain Size of the Inorganic Granular Material>

There is no specific limitation on the grain size and the grain size distribution of the inorganic granular material (C) that is used for the dental curable composition of the present invention. Preferred grain size of the inorganic granular material lies in a range of 0.001 to 50 µm. The filling rate of the inorganic material can be increased by densely filling the granular material. It is, therefore, desired that the grain size distribution is the one that includes those of an inorganic granular material (C-1) having a mean grain size of 1 to 50 µm (hereinafter often referred to as inorganic granular material of the order of microns), an inorganic granular material (C-2) having a mean grain size of 0.1 to less than 1 µm (hereinafter often referred to as inorganic granular material of the order of submicrons), and an inorganic granular material (C-3) having a mean grain size of 0.001 to less than 0.1 µm (hereinafter often referred to as inorganic granular material of the order of nanometers).

A grain size distribution of the type of multiplicity of peaks in which the granular materials of the respective orders of grain sizes have their respective peaks, is preferred to a grain size distribution of the type of a single peak having only one peak from the standpoint of increasing the filling rate. Further, the smaller the amount of coarse particles, the larger the strength and the better the abrasiveness. It is, therefore, desired that the granular materials have grain sizes of less than 10 µm at 90% in the volume-based cumulative grain size distribution and, more preferably, less than 7 µm at 90% in the volume-based cumulative grain size distribution.

As the inorganic granular material (C-1) of the order of microns, there is preferably used a granular material of amorphous shape, plate-like shape, aggregated shape or clustered shape to attain a large strength. The granular materials of the aggregated shape and clustered shape are produced by aggregating the inorganic granular material (C-2) of the order of submicrons or the inorganic granular material (C-3) of the order of nanometers followed, as required, by the heat treatment or the coagulation treatment. It is estimated that the inorganic granular materials of the above-mentioned shapes have an effect of preventing the cracks from spreading when they are broken. It is, therefore, considered that the granular materials of the above-mentioned shapes make it possible to attain larger strengths.

The material (C-1) has a mean grain size of, preferably, 1 to 9 µm and, particularly preferably, 2 to 5 µm. The material (C-1) having a too large mean grain size may cause a decrease in the abradability of the cured body of the dental curable composition. The material (C-1) should, preferably, contain the granular material of a grain size of not less than 10 µm in an amount of not more than 3% by mass and, preferably, not more than 1% by mass. Coarse particles of not smaller than 10 µm when contained in large amounts could trigger the breakage and could decrease the strength.

From an image taken through an electron microscope of the scanning type or the transmission type, a mean grain size of the inorganic granular material in the present invention refers to the size measured by analyzing the image of circle equivalent diameter (diameter of a circle having the same area as the area of the grain to be measured) of the primary grain size. The image for measurement taken through the electron microscope is the one that has distinct brightness and darkness, and that enables contours of the grains to be discerned. The image is analyzed by using an image analyzing software that is capable of at least measuring the area of the grain, maximum length and minimum width of the grain. A mean grain size and a mean uniformity of the primary grains are calculated in compliance with the following formula from the primary grain size measured above.

$$\text{Mean grain size: } X = \sqrt[3]{\frac{\sum_{i=1}^{n} X_i^3}{n}} \quad \text{[Mathematical 1]}$$

(mean volume size)

n: number of grains observed,
Xi: grain size (diameter) of the i-th grain.

$$\text{Mean uniformity} = \frac{\sum_{i=i}^{n} Bi/Li}{n} \quad \text{[Machematical 2]}$$

Here, the number of grains is (n), a maximum length of the grain is the long diameter (Li), and a diameter in the direction at right angles with the long diameter is the minimum width (Bi). In calculating these values, it is necessary to measure at least not less than 40 grains to maintain precision of measurement, and it is desired to measure not less than 100 grains.

The inorganic granular material (C-2) of the order of submicrons is, preferably, the granular material of the spherical shape or the nearly spherical shape to attain a high filling rate. The nearly spherical shape referred to here stands for a shape having a mean uniformity of not less than 0.6 as found by analyzing the image taken through the electron microscope of the scanning type or the transmission type. The mean uniformity should be, preferably, not less than 0.7 and, more preferably, not less than 0.8. A preferred mean grain size is 0.1 to 0.6 µm and, specifically, 0.3 to 0.5 µm.

The inorganic granular material (C-3) of the order of nanometers is, preferably, the granular material of the spherical shape or the nearly spherical shape to attain a high filling rate. The nearly spherical shape referred to here stands for a shape having a mean uniformity of not less than 0.6 as found by analyzing the image taken through the electron microscope of the scanning type or the transmission type. The mean uniformity should be, preferably, not less than 0.7 and, more preferably, not less than 0.8. A preferred mean grain size is 0.01 to 0.09 µm and, specifically, 0.05 to 0.08 µm.

The materials (C-1), (C-2) and (C-3) can be blended at any ratio without limitation. Preferably, however, when the amount of the inorganic granular material (C) as a whole is set to be 100% by mass, the material (C-1) should be 30 to 80% by mass and, more preferably, 40 to 70% by mass, the material (C-2) should be 10 to 50% by mass and, more preferably, 20 to 40% by mass, and the material (C-3) should be 0 to 30% by mass and, more preferably, 10 to 20% by mass.

The inorganic granular material (C) may further contain other inorganic granular materials than the materials (C-1), (C-2) and (C-3) but in amounts in a range in which they will not impair the effects of the present invention.

<Method of Producing Inorganic Granular Materials>

The inorganic granular material (C) can be the one produced by any known method. The inorganic granular material can be, for example, an inorganic oxide or a composite oxide produced by any method such as wet method, dry method, melting method or sol-gel method, further, followed by such treatments as pulverization, digestion, drying, coagulation, heating, firing and cooling. When it is attempted to obtain the granular material in an aggregated form or a clustered granular form, aggregation or clustering is executed by dispersing the inorganic granular material in a suitable solvent and, thereafter, distilling off the solvent. Or the inorganic granular material is heated at a temperature of not lower than 100° C., calcined or formed by applying pressure. Or by using a binder in a suitable small amount, the inorganic granular material is formed into aggregated masses thereof. As required, further, the aggregated masses are pulverized and classified so as to possess desired grain sizes. Moreover, as required, the granular material may be subjected to a silane coupling treatment to treat the surfaces thereof. Otherwise, the inorganic granular material may be heated at a temperature of not lower than 100° C. so that the primary grains are strongly aggregated together. The inorganic granular material obtained by the above-mentioned methods may be fired at a temperature of 500 to 1000° C. to impart surface stability. The firing is effective in reducing active groups such as silanol groups on the surfaces of the inorganic granular material and, therefore, works to suppress a decrease in the strength after dipped in water. During the firing, the inorganic granular material may often be partly aggregated. In such a case, the aggregated grains are digested into primary grains by using a jet mill or a vibrating ball mill and, further, the grain size is so adjusted as to lie within a predetermined range. Through the above treatment, abrasiveness of the composition can be improved when the composition is used as a dental composition.

<Treating the Surfaces of the Inorganic Granular Material>

The inorganic granular material (C) is desirably treated for its surfaces with a surface-treating agent in order to improve wettability for the polymerizable monomer (A), to develop covalent bond with the polymerizable monomer, to improve the strength and to suppress a decrease in the strength after dipped in water.

There can be used any surface-treating agent that has been known per se. Preferred examples of the surface-treating agent are such silane coupling agents as:

Vinyltriethoxysilane,
Vinyltrimethoxysilane, Vinyl-tris(β-methoxyethoxy)silane,
γ-Methacryloyloxypropyltrimethoxysilane,
κ-Methacryloyloxydodecyltrimethoxysilane,
β-(3,4-Epoxycyclohexyl)-ethyltrimethoxysilane,
γ-Glycidoxypropyl-trimethoxysilane,
N-β-(aminoethyl)-γ-aminopropyl-trimethoxysilane,
γ-Ureidopropyl-triethoxysilane,
γ-Chloropropyltrimethoxysilane,
Methyltrimethoxysilane,
Ethyltrimethoxysilane, and
Methyltriethoxysilane.

It is specifically desired to use a silane coupling agent having an aromatic ring and a silane coupling agent having a fluoroalkyl group from the standpoint of high water-proof property. Concrete examples of such silane coupling agents are:

3-(4-Methacryloyloxyphenyl)propyltrimethoxysilane, and

Polyfluoroalkyltrimethoxysilane.

Depending upon the inorganic granular material that is used, furthermore, it would often be more desirable to use an aluminate type coupling agent, a titanate type coupling agent or a zirconate type coupling agent. These optimum surface-treating agents can be suitably selected while evaluating their properties.

There is no specific limitation on the amount of the surface-treating agent used for treating the surfaces of the inorganic granular material (C), and an optimum amount should be selected relying on the results of some preliminary experiments. The surface-treating agent used in either too large amounts or too small amounts could lower the strength after dipped in water. The amount of the surface-treating agent that is used is, preferably, 1 to 30 parts by mass per 100 parts by mass of the inorganic granular material (C).

There is no specific limitation on the method of treating the surfaces, and any known method can be used without limitation. A representative treating method consists of dispersing and mixing the inorganic granular material (C) and the surface-treating agent together in a suitable solvent by using a ball mill or the like, followed by drying in the air or by using an evaporator and, thereafter, heating the mixture thereof at 50 to 150° C. A method can be, further, exemplified consisting of heating and refluxing the inorganic granular material (C) and the surface-treating agent in a solvent such as alcohol for about several hours. There can be, further, exemplified a method of graft-polymerizing the surface-treating agent on the surfaces of the granular material, and a method of integrally blending the materials together.

When there is used an aggregated or clustered granular material that is produced by aggregating the inorganic granules as the inorganic granular material (C) and, as required, subjecting the inorganic granular material (C) to the heat treatment or the aggregating treatment, the above-mentioned surface treatment may be executed for either the primary grains or the aggregated grains. For example, when the aggregated granules are produced by spray-drying, the surface treatment should be executed simultaneously with the spray-drying to improve the efficiency.

<Other Arbitrary Components>

The dental curable composition of the present invention is allowed to contain any components in addition to containing (A) the radically polymerizable monomer component, (B) the polymerization catalyst, and (C) the inorganic granular material. For example, there can be contained a polymerization inhibitor, chain transferring agent, fluorescent agent, ultraviolet ray absorber, antioxidant, pigment, antibacterial agent and X-ray contrasting agent. These arbitrary components can be the known ones that have been used for the dental curing compositions.

<Method of Preparing the Dental Curable Composition>

The dental curable composition of the present invention can be prepared by a known method. Usually, the above-mentioned essential components and the components to be arbitrarily added as required are provided in predetermined amounts, kneaded together to a sufficient degree, and the paste thereof is defoamed to obtain the dental curable composition.

<Use of the Dental Curable Composition>

There is no specific limitation on the use of the dental curable composition of the present invention. Namely, the dental curable composition can be favorably used as dental restorative materials and dental prosthetic materials like composite resin, hard resin, artificial teeth, cement, and resin type material that is to be used by being cut.

The cured body of the dental curable composition of the invention is the one that is obtained by polymerizing and curing the dental curable composition. The dental curable composition may be provided in its own form, such as composite resin, hard resin or cement when the shape is to be formed by the user on the site and is polymerized and cured by a suitable polymerizing method. Or the dental curable composition may be provided in the form of a cured body thereof like a dental resin that is to be cut when a desired shape is to be formed by cutting a block of the cured body.

The cured body of the dental curable composition of the present invention should have a bending strength of, preferably, not less than 220 MPa, more preferably, not less than 240 MPa and, most preferably, not less than 250 MPa after it was dipped in water of 37° C. for 7 days. The ratio of the bending strength of the cured body of the invention after it was dipped in water of 37° C. for 7 days to the initial bending strength thereof should be, desirably, not less than 90%, more desirably, not less than 95% and, most desirably, not less than 98%. The method and conditions for measuring the bending strengths are as described in Examples appearing later.

<The Resin Type Dental Material that is to be Used by Being Cut>

The cured body of the dental curable composition of the invention has a large initial strength, suppresses a decrease in the strength after it is dipped in water and, therefore, is preferably used as a resin type dental material that is to be cut in a use where the dental material must have a particularly large strength. The feature of the cutting work is that it is capable of mechanically cutting even those materials that have a large strength and hardness. The dental resin material of the present invention is used by being cut. That is, concretely speaking, the dental resin material of the invention can be favorably used as a material for making denture, denture base, artificial tooth, implant fixture, abutment, superstructure, inlay, onlay, crown, bridge, abutment structure and the like. Specifically, the dental resin material of the present invention is used by being cut, i.e., is used as a material for making crown and bridge on account of its large initial strength as well as its large strength even after dipped in water.

It is desired that the dental resin material that is to be used by being cut of the invention is worked into a suitable size so that it can be set to a dental CAD/CAM system that is placed in the market. Desired sizes are, for example, a prism measuring 40 mm×20 mm×15 mm that is suited for fabricating a one tooth missing bridge; a prism measuring 17 mm×10 mm×10 mm suited for fabricating an inlay or an onlay; a prism measuring 14 mm×18 mm×20 mm, 10 mm×12 mm×15 mm or 14.5 mm×14.5 mm×18 mm suited for fabricating a full crown; and a disc of a diameter of 90 to 100 mm and a thickness of 10 to 28 mm suited for fabricating a long span bridge and a denture base, though the dental resin material to be to be used being cut is in no way limited thereto only.

The dental resin material to be used by being cut of the invention may be fitted with a fixture for fixing to the cutting machine. There is no specific limitation on the fixture provided it is of such a shape that can be connected to the cutting machine. The material of the fixture will be a stainless steel, brass or aluminum. The fixture can be attached to the dental resin material that is to be used by being cut by such a method as adhesion, fitting, or using screw. There is no specific limitation, either, on the method of adhesion, and there can be used various adhesives placed in the market, such as those of the isocyanate type, epoxy type, urethane type, silicone type and acrylic type.

There is no specific limitation on the method of producing the dental resin material that is to be used by being cut of the present invention from the dental curable composition, and a suitable production method may be selected and employed depending on the object and the material that is used. For example, the radically polymerizable monomer component (A) will be blended with the polymerization catalyst (B), inorganic granular material (C) and other arbitrary components, followed by stirring, kneading, dissolving, dispersion, metering, filling into a mold, defoaming and forming. As required, furthermore, the composition thereof will be false-polymerzed with heat or light. Thereafter, energy will be imparted externally, such as using a thermal polymerization initiator depending upon the initiation mechanism of the polymerization catalyst (B). In such a case, the composition is polymerized and cured by heating or, as required, by heating with pressure using nitrogen to produce the dental resin material that is to be used by being cut. Thereafter, the obtained dental resin material to be used by being cut can also be subjected to the after treatments such as polishing, leveling, printing and heat treatment.

Described below is a method of fabricating a work from the dental resin material that is to be used by being cut of the present invention.

First, a dentist forms an abutment in the oral cavity of a patient. For instance, a tooth is ground to form the abutment. Next, the dentist picks up the impression of the abutment, neighboring tooth and opposing tooth. The impression is picked up by using an alginate impression material, a silicone impression material or a digital impression device. Thereafter, the dental technician or the dentist prepares a gypsum model from the impression that is picked up, and digitizes the form of the gypsum model by using a scanning machine. Or a digital model is fabricated from the data that are picked up from the digital impression.

Next, digital data of a prosthetic are prepared based on the data measured from the clay model by using a design software. Digital data for cutting with the cutting machine are prepared based on the digital data of the prosthetic. At this moment, desirably, it is confirmed on the software that the portion to be cut of the present invention has a size large enough for preparing the prosthetic.

Thereafter, the dental block to be cut of the invention is set on the cutting machine, and the cutting work is executed. It is desired to use a dental cutting machine that is available in the market. To execute the cutting work, it is necessary to use a cutting tool (bar) and a cutting (CAM) software. The CAM software controls the motion of the cutting tool and the motion of the block that is fixed via the fixture. Representative parameters include position data, feed speed, revolving speed, etc. The cutting tool is, desirably, a generally employed dental cutting bar. The cutting tool should, desirably, have a coating such as diamond coating to cope with the abrasion. Usually, the cutting bar includes a plurality of cutting bars in combination to meet the steps of cutting, such as rough cutting, intermediate cutting, fine cutting, etc. Briefly speaking, a crown form is roughly formed by using a roughly cutting bar (e.g., 2 mm in diameter) and, thereafter, the surface is smoothed or a fine structure such as of occlusion surface is expressed by using a finely cutting bar (e.g., 0.8 mm in diameter). After the cutting work with the cutting machine has been finished, a sprue portion is separated away from the dental block that is cut. After the form is corrected and polished, the inner surface of the prosthetic is, as required, pre-treated (roughened with sand blast, etc.). The thus prepared prosthetic is, as required, pre-treated (application of a primer, etc.) for the inner surface thereof, and is adhered to the abutment in the oral cavity of the patient.

EXAMPLES

The invention will be described more concretely by using Examples to which only, however, the invention is no way limited. Described below are the materials used in Examples and Comparative Examples, as well as testing methods.
<Radically Polymerizable Monomer Components (A)>
Bifunctional monomer (A-1)
  HD: 1,6-Hexanediol dimethacrylate
  NPG: Neopentyl glycol dimethacrylate
  DCP: Tricyclodecanedimethanol dimethacrylate
  ND: 1,9-Nonanediol dimethacrylate
Diluting monomer (A-2)
  TEGDMA: Triethylene glycol dimethacrylate
Basic monomer (A-3)
  UDMA: 1,6-Bis(methacrylethyloxycarbonylamino)-trimethylhexane
  D-2.6E: 2,2-Bis(4-methacryloyloxyethoxyphenyl) propane (ethylene oxide, 2.6 mols)
<Polymerizing Catalyst (B)>
  BPO: Benzoyl peroxide
<Inorganic Granular Material (C)>
Inorganic Granular Material (C) of the Order of Microns (C-1-1) A product obtained by treating an amorphous silica-zirconia having a mean grain size of 3.5 μm with a γ-methacyloyloxypropyltrimethoxysilane.

(C-1-2) An aggregated granular material having a mean grain size of 12 μm. That is, a silica-zirconia of a spherical shape having a mean grain size of 0.2 μm was treated with the γ-methacryloyloxypropyltrimethoxysilane and was spray-dried. 100 Parts by mass of the thus obtained aggregated product was imbibed with 17 parts by mass of a curable composition and was, thereafter, cured by being thermally polymerized to obtain the above aggregated granular material having a mean grain size of 12 μm. The curable composition was used as a binder, and contained 0.5 parts by mass of BPO per 100 parts by mass of the mixture of 75 parts by mass of UDMA and 25 parts by mass of HD.

(C-1-3) An aggregated granular material having a mean gran size of 12 μm obtained by heat-treating (calcining) a spray-dried aggregate of silica-zirconia of a spherical shape having a mean grain size of 0.2 μm at 550° C. for 4 hours and was, thereafter, treating the surfaces thereof with the γ-methacryloyloxypropyltrimethoxysilane.
Inorganic Granular Material (C-2) of the Order of Submicrons (C-2-1) A product obtained by treating a silica-zirconia of a spherical shape having a mean grain size of 0.4 μm with the γ-methacyloyloxypropyltrimethoxysilane.

(C-2-2) A product obtained by treating a silica-zirconia of a spherical shape having a mean grain size of 0.2 μm with the γ-methacyloyloxypropyltrimethoxysilane.

Inorganic Granular Material (C-3) of the Order of Nanometers (C-3-1) A product obtained by treating a silica-titania of a spherical shape having a mean grain size of 0.08 μm with the γ-methacyloyloxypropyltrimethoxysilane.

(C-3-2) Fumed silica having a mean grain size of 15 nm.

<Mean Grain Sizes of the Inorganic Granular Materials>

By using a scanning type electron microscope (XL-30S manufactured by Phillips Co.), the inorganic particles were photographed at a magnifying power of 5,000 to 100,000 times. By using an image analysis software (IP-1000PC, trade name; produced by Asahi Kasei Engineering Co.), the photographed images were processed. The number of particles (100 or more) observed in a unit visual field of the photograph and circle equivalent diameters of the primary particles were measured. A mean grain size was calculated in compliance with the above-mentioned formula based on the measured values.

<Grain Size of the Inorganic Granular Material at 90% in the Volume-Based Cumulative Grain Size Distribution>

0.1 Grams of an inorganic granular material was dispersed in 10 ml of ethanol and was irradiated with ultrasonic waves for 20 minutes. By using a grain size distribution meter (LS230 manufactured by Beckman Coulter Co.) based on the laser diffraction/light scattering method, the grain size (D90) was found at 90% in the volume-based cumulative grain size distribution by adopting an optical model (Fraunhofer).

<Bending Test>

Twenty test pieces each measuring 1.2 mm×4.0 mm×18 mm were cut out from the cured body of the dental curable composition, and the surfaces thereof were each finished by using a P2000 water-proof polishing paper. The thus obtained test pieces were dipped in the purified water and were stored in a constant temperature oven maintained at 37° C. for 7 days. By using a universal testing machine, autograph (manufactured by Shimazu Mfg. Co.), the 4.0 mm×18 mm surfaces were subjected to the three point bending test under the conditions of an atmosphere of room temperature, a distance between the fulcrums of 12.0 mm and a crosshead speed of 1.0 mm/min. Bending strengths [MPa] were calculated according to the following formula from the 10 test pieces before dipped in water and from another 10 test pieces after dipped in water to find mean values.

Bending strength [MPa]=$3FS/(2bh^2)$ where, F: maximum load [N] exerted on the test piece, S: distance between the fulcrums [mm], b: width [mm] of the test piece measured just before the test, h: thickness [mm] of the test piece measured just before the test.

From the thus found strengths, there were calculated the bending strengths of the cured bodies of the invention relative to the initial bending strengths thereof (bending strength ratios).

Example 1

15 Parts by mass of HD, 15 parts by mass of UDMA, 70 parts by mass of D-2.6E, and 1.0 part by mass of BPO were mixed together to prepare a curable and polymerizable monomer composition. Further, 60 parts bymass of (C-1-1), 28 parts bymass of (C-2-1) and 12 parts by mass of (C-3-1) were mixed together to prepare an inorganic granular composition. The above curable and polymerizable monomer composition was added in an amount of 16% by mass to 84% by mass of the above inorganic granular composition. The two compositions were mixed by using a planetary mixer until they became homogeneous and paste-like consistency which was then defoamed in vacuum to prepare a dental curable composition. The dental curable composition was filled in a mold of 14.5 mm×14.5 mm×18 mm and was heated at 120° C. for 2 hours under a nitrogen pressure of 0.4 MPa so as to be polymerized and cured. A cured body of the dental curable composition was thus obtained and was subjected to the bending test. Table 1 shows the results of the bending test.

Examples 2 to 12

Cured bodies were prepared by the same method as that of Example 1 but changing the polymerizable monomer (A) and the inorganic granular composition (C) and also changing the blending ratios into those described in Table 1, and were subjected to the bending test. The results were as shown in Table 1.

Comparative Examples 1 to 3

Cured bodies were prepared by the same method as that of Example 1 but changing the polymerizable monomer (A) and the inorganic granular composition (C) and also changing the blending ratios into those described in Table 1, and were subjected to the bending test. The results were as shown in Table 1.

TABLE 1

| | Polymerizable monomer (A) (mass %) | | | Polymerizing | Inorganic granular material (C) (mass %) | | |
|---|---|---|---|---|---|---|---|
| | (A-1) | (A-2) | (A-3) | catalyst (B) | (C-1) | (C-2) | (C-3) |
| Example 1 | HD(15) | — | D-2.6E(70) UDMA(15) | BPO(1.0)*1 | (C-1-1) 60% | (C-2-1) 28% | (C-3-1) 12% |
| Example 2 | NPG(15) | — | D-2.6E(70) UDMA(15) | BPO(1.0) | (C-1-1) 60% | (C-2-1) 28% | (C-3-1) 12% |
| Example 3 | NPG(15) | — | D-2.6E(70) UDMA(15) | BPO(1.0) | (C-1-1) 60% | (C-2-1) 28% | (C-3-1) 12% |
| Example 4 | DCP(15) | — | D-2.6E(70) UDMA(15) | BPO(1.0) | (C-1-1) 60% | (C-2-1) 28% | (C-3-1) 12% |
| Example 5 | ND(15) | — | D-2.6E(70) UDMA(15) | BPO(1.0) | (C-1-1) 60% | (C-2-1) 28% | (C-3-1) 12% |
| Example 6 | NPG(30) | — | UDMA(70) | BPO(1.0) | (C-1-1) 60% | (C-2-1) 28% | (C-3-1) 12% |
| Example 7 | NPG(25) | TEGDMA(5) | UDMA(70) | BPO(1.0) | (C-1-1) 60% | (C-2-1) 28% | (C-3-1) 12% |
| Example 8 | NPG(40) | — | UDMA(60) | BPO(1.0) | (C-1-1) 60% | (C-2-1) 28% | (C-3-1) 12% |

TABLE 1-continued

| | | | | | | | |
|---|---|---|---|---|---|---|---|
| Example 9 | NPG(5) | — | D-2.6E(35) UDMA(60) | BPO(1.0) | (C-1-1) 60% | (C-2-1) 28% | (C-3-1) 12% |
| Example 10 | DCP(20) | — | UDMA(80) | BPO(1.0) | (C-1-1) 60% | (C-2-1) 28% | (C-3-1) 12% |
| Example 11 | DCP(20) | — | UDMA(80) | BPO(1.0) | (C-1-2) 50% | (C-2-2) 49% | (C-3-2) 1% |
| Example 12 | DCP(20) | — | UDMA(80) | BPO(1.0) | (C-1-3) 60% | (C-2-1) 28% | (C-3-1) 12% |
| Comparative Example 1 | — | TEGDMA(15) | D-2.6E(70) UDMA(15) | BPO(1.0) | (C-1-1) 60% | (C-2-1) 28% | (C-3-1) 12% |
| Comparative Example 2 | — | TEGDMA(30) | UDMA(70) | BPO(1.0) | (C-1-1) 60% | (C-2-1) 28% | (C-3-1) 12% |
| Comparative Example 3 | HD(50) | — | UDMA(50) | BPO(1.0) | (C-1-1) 60% | (C-2-1) 28% | (C-3-1) 12% |

| | Inorganic granular material D90 | Inorganic granular material filling rate | Bending strength [MPa] Initially | Bending strength [MPa] After having absorbed water | Ratio of bending strengths |
|---|---|---|---|---|---|
| Example 1 | 6 μm | 84% | 255 | 243 | 95% |
| Example 2 | 6 μm | 84% | 266 | 258 | 97% |
| Example 3 | 9 μm | 82% | 259 | 248 | 96% |
| Example 4 | 6 μm | 84% | 252 | 249 | 99% |
| Example 5 | 6 μm | 84% | 248 | 231 | 93% |
| Example 6 | 6 μm | 84% | 249 | 237 | 95% |
| Example 7 | 6 μm | 84% | 248 | 225 | 91% |
| Example 8 | 6 μm | 84% | 231 | 223 | 97% |
| Example 9 | 6 μm | 84% | 261 | 235 | 90% |
| Example 10 | 6 μm | 84% | 250 | 241 | 96% |
| Example 11 | 12 μm | 81% | 238 | 235 | 99% |
| Example 12 | 15 μm | 82% | 245 | 241 | 98% |
| Comparative Example 1 | 6 μm | 84% | 257 | 209 | 81% |
| Comparative Example 2 | 6 μm | 84% | 256 | 206 | 80% |
| Comparative Example 3 | 6 μm | 84% | 213 | 190 | 89% |

*1Parts by mass per 100 parts by mass of the polymerizable monomer (A). Table 1 to be continued.

The invention claimed is:

1. A dental curable composition which includes a radically polymerizable monomer component (A) consisting of a bifunctional monomer component (A-1), a basic monomer component (A-3) and optionally a diluting monomer component (A-2); a polymerizing catalyst (B); and an inorganic granular material (C), characterized in that:

said bifunctional monomer (A-1) is represented by a following formula (α), $$R_P-SP^1-R_P \quad (α)$$

where, $R_P$ is a radically polymerizable group represented by $CH_2=C(R)-COO-$ or $CH_2=C(R)-CONH-$, wherein R is a hydrogen atom or a hydrocarbon group having 1 to 3 carbon atoms, and $SP^1$ is a hydrocarbon group having 5 to 15 carbon atoms;

a content of said bifunctional monomer (A-1) in the radically polymerizable monomer component (A) is 10 to 20% by mass under a condition that the content of the diluting monomer (A-2), relative to the monomer component (A), is zero or not more than 5% by mass, the diluting monomer (A-2) being represented by a following formula (β), $$R_P-SP^2-R_P \quad (β)$$

where, $R_P$ is as defined in the above formula (α), and $SP^2$ is an aliphatic hydrocarbon group different from $SP^1$, an oxygen-containing aliphatic hydrocarbon group having not less than 2 oxygen atoms, or an oxygen-containing aromatic hydrocarbon group having not less than 3 oxygen atoms;

said basic monomer (A-3) is a radically polymerizable monomer other than (A-1) or (A-2) and containing 2 to 6 radically polymerizable groups and, further, having, a molecular structure in which the radically polymerizable groups are coupled together via a crosslinking group that has an aromatic ether bond, an aromatic ketone bond, an amide bond or an urethane bond;

said inorganic granular material (C) is contained in an amount of 400 to 700 parts by mass per 100 parts by mass of the radically polymerizable monomer component (A); and said polymerizing catalyst (B) is a thermally polymerizing catalyst.

2. The dental curable composition according to claim 1, wherein in said bifunctional monomer (A-1), said group $SP^1$ has a hydrocarbon group on a side chain thereof.

3. The dental curable composition according to claim 1, wherein in said bifunctional monomer (A-1), the group $SP^1$ has an aliphatic hydrocarbon ring or an aromatic ring on a main chain thereof.

4. The dental curable composition according to claim 1, wherein the content of the diluting monomer (A-2) is zero.

5. The dental curable composition according to claim 1, wherein said polymerizing catalyst (B) is contained in an amount of 0.01 to 5 parts by mass per 100 parts by mass of said radically polymerizable monomer component (A).

6. A cured body of the dental curable composition of claim 1.

7. The cured body according to claim 6, wherein the cured body is used as a dental resin that is to be used by being cut.

8. The cured body according to claim 7, wherein the cured body has a bending strength of not less than 220 MPa after it is dipped in water of 37° C. for 7 days.

9. The cured body according to claim 8, wherein the cured body, after it is dipped in water of 37° C. for 7 days, has a bending strength which is not less than 95% of the initial bending strength thereof.

10. The dental curable composition according to claim 1, wherein the bifunctional monomer component (A-1) is at least one selected from a group consisting of 1,5-pentanediol di(meth)acrylate, 1,6-hexanediol di(meth)acrylate, 1,9-nonanediol di(meth)acrylate, 1,10-decanediol di(meth)acrylate, neopentyl glycol di(meth)acrylate, tricyclodecanedimethanol di(meth)acrylate and 2,2-bis((meth)acryloyloxyphenyl)propane.

* * * * *